United States Patent [19]

Sauerwein et al.

[11] Patent Number: 4,975,934
[45] Date of Patent: Dec. 4, 1990

[54] PROCESS AND DEVICE FOR PRODUCING A RADIOGRAPHIC IMAGE

[75] Inventors: Kurt Sauerwein, Erkrath; Rainer Link, Kerpen-Horrem; Wolfgang Nuding, Troisdorf; Helmut Wiacker, Hilden; Wolfgang Zindler, Dormagen; Thomas Monsau, Düsseldorf-Oberkassel, all of Fed. Rep. of Germany

[73] Assignee: Dr. Kurt Sauerwein, Haan, Fed. Rep. of Germany

[21] Appl. No.: 298,038

[22] Filed: Jan. 17, 1989

[30] Foreign Application Priority Data
Feb. 3, 1988 [DE] Fed. Rep. of Germany ....... 3803129

[51] Int. Cl.$^5$ ............................................ G01N 23/00
[52] U.S. Cl. ........................................ 378/20; 378/19
[58] Field of Search ................................ 378/20, 19, 4

[56] References Cited

U.S. PATENT DOCUMENTS 4,164,657 8/1979 Duinber et al. .................. 378/19
4,570,264 2/1986 Liebitruth ........................ 378/20

Primary Examiner—Craig E. Church
Attorney, Agent, or Firm—Toren, McGeady & Associates

[57] ABSTRACT

A process and device for producing a radiographic image of a body employ a source of high-energy radiation arranged on one side of the body and a pick-up device arranged on the other side of the body, a real-time system for reproducing the radiographic image having a television camera and a screen, and a computer-tomograph to evaluate the radiographic image row-wise and to display a cross-section of the radiographed body on the screen. By means of the real-time radiographic image a cross-section is selected and represented computer-tomographically. In this manner in the real-time radiographic image the location can be determined of which a layer image is necessary in order to recognise defects in the body being radiographed.

16 Claims, 3 Drawing Sheets

PROCESS AND DEVICE FOR PRODUCING A RADIOGRAPHIC IMAGE

TECHNICAL FIELD OF THE INVENTION AND PRIOR ART

The invention relates to a process and a device for producing a radiographifc image of a body, having a source of high-energy radiation arranged on one side of the body and a pick-up device for the radiographic image arranged on the other side of the body, in particular for use in non-destructive testing of materials.

A device for non-destructive radiographic testing is known from DE-OS No. 35 20 600 in which radiation from an X-ray or gamma ray source passes through a workpiece arranged between the radiation source and a luminescent screen to produce a radiographic image on the luminescent screen that is displayed on a television monitor by transmission by means of a closed circuit television system. The radiographic image is reproduced in real time and is a shadow image which shows variations in density or thickness as different degrees of lightness. In the case of non-destructive radiographic testing of workpieces, very large differences in thickness very often occur side by side, for example in the case of engine blocks, weld beads and other complex components. Since in such different wall thicknesses, often very close to one another, even very small defects have to be made visible, the range of contrast necessary for the image-forming system is very wide. Owing to the often great differences in thickness within an image, the areas where the wall thickness is smaller or where material is missing are so heavily over-radiated that on the one hand damage to the television camera tube can occur and on the other hand the degree of contrast that is technically possible is not sufficient to make small differences, which indicate small defects, visible. It is therefore difficult to arrive at a quick and exactly localised indication of defects in the item tested.

A radiographic process and a radiographic device for testing materials are known from DE-OS No. 32 24 964, in which a high resolution radiation detector and a radiation source are arranged to be rotated relative to the item to be tested by means of a rotatable object carrier in a plane that includes the radiation source and the radiation detector and about an axis normal thereto. At each angle of rotation the spatial distribution of the intensity of radiation is calculated by means of an electronic evaluating device. In this manner a plurality of measurements are made at different angles of rotation in a thin layer which is determined by said plane that includes the radiation source and the radiation detector, and a linear radiation projection is calculated in each case. In an electronic computer these different projections are processed by logarithmation, folding and unfolding in the manner known from computer-tomography to produce a layer image of the item being tested, which is subsequently displayed on a screen or stored elsewhere.

With this process thin layers of material can be examined for radiation attenuation and all details of the layer image can be reproduced with high resolution. However, a considerable amount of time is needed to produce a layer image, since each time revolution through 1° to 2° is necessary through an angular range of at least 180°. Editing the radiographic data in the computer also requires a fairly long time since the calculating operations are very time consuming and complicated. In order to thoroughly examine a body that is critical with regard to safety, layer images have to be made every few millimeters, and hence computer-tomography is only used in exceptional cases for non-destructive testing of materials.

OBJECT OF THE INVENTION

It is the object of the invention to provide a process and a device for producing a radiographic image with which it is possible to test a body for defects relatively quickly but nevertheless with great accuracy.

BRIEF DESCRIPTION OF THE INVENTION

This object is achieved according to the invention with a device of the kind mentioned in the introduction by combining a real-time system for showing the radiographic image with a television camera, a screen and a computer-tomograph to evaluate the radiographic image row-wise and to display a cross-section of the radiographed body on the screen.

With this combination it is possible first to view on the television screen the radiographic image of the body to be tested as a whole and then to determine which layers are to be displayed on the screen by means of the computer-tomograph so as to provide a detailed cross-section of the body being inspected in which possible faults can be recognised with great accuracy. In this manner the number of necessary layer images is reduced to that absolutely essential and the examination is considerably speeded up.

The device for picking up the radiographic image can comprise a radiographic image amplifier followed by a television camera. Alternatively the device for picking up the radiographic image can comprise an X-ray image screen followed by a light amplifier and a television camera.

To produce the layer image a high resolution row-detector can be arranged in the beam path of the radiographic image, in which case the television camera and/or the row-detector can be movable, or alternatively the radiographic image may be directed towards the television camera or towards the row-detector by means of a movable mirror. Finally it is also possible to arrange a semi-transparent mirror in the beam path of the radiographic image and to direct the transmitted or reflected image towards the television camera or the row-detector.

If a high resolution row-detector is used to provide the data for the layer image, what is required is either a radiation source that is rotatable and adjustable in height relative to the body and a monitoring device, or a rotatable and height-adjustable manipulator for the body to be radiographically inspected, or a rotatable manipulator for the body to be radiographically tested and a height-adjusting device for the row-detector and the radiation source, in order to adjust the body relative to the radiation source and to the pick-up system or to the row-detector. The television image is preferably used directly so as to provide the data for the computer-tomograph. For this purpose an image store is arranged after the television camera, and the computer-tomograph is connected to the image store for row-wise evaluation of the image. In this case the body to be inspected need only be rotated stepwise by means of the manipulator while a desired row of the television image is selected by the operator and input in order to produce the layer image therefrom.

In order to specify a particular layer for computer-tomographic representation of a layer image, row markings can be arranged on the screen, and a selected row marking can then be input into a row-selecting device which is connected to the height-adjusting device of the manipulator, of the row-detector or of the radiation source or to the image store.

It is however also possible to use a purely electronic row-selecting device if an image processing device is arranged between the television camera and the screen. In this case the row-selecting device is connected to the image processing device and to the height-adjusting device of the manipulator or of the row-detector or to the image processing device and the image store.

In the process according to the invention for producing a radipgraphic image of a body, a radiographic image is produced on a screen by means of a real-time reproducing system, a row is selected with reference to the displayed image for showing a computer-tomographical layer image and is input, and the computer-tomographical measurements are carried out by rotating the body stepwise. The data are stored and edited and the image is reconstructed and displayed on a screen. The image points of the television image are preferably stored in a two-dimensional image store and the image points of each row are reconstructed by a computer-tomograph to form a layer image of this row.

BRIEF DESCRIPTION OF THE DRAWINGS

The invention will now be explained in more detail with reference to several exemplary embodiments shown in the drawings, in which.

DETAILED DESCRIPTION OF PREFERRED EMBODIMENTS OF THE DRAWINGS

Figure 1:
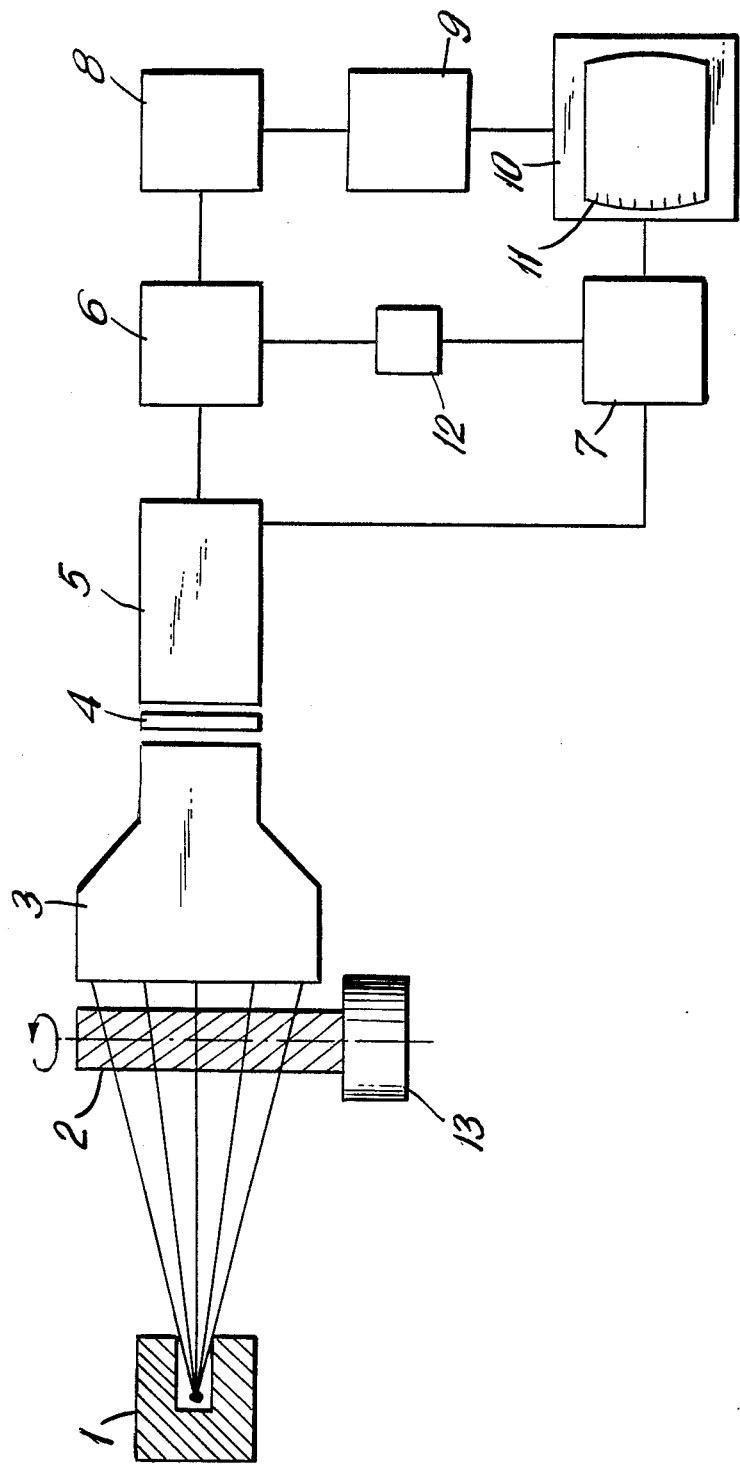
FIG. 1 is a diagram showing the functioning of the device according to the invention having an X-ray image amplifier followed by a television camera, and a side elevation of the body to be inspected.

By means of a radiation source 1, which can comprise an X-ray tube or a gamma-radiator, high-energy radiation is transmitted through a body 2 to be inspected. The body 2 is rotatably arranged on a manipulator 13. In the beam path of the radiation source 1 there is an X-ray image amplifier 3 whose image reaches a television camera 5 via a lens 4. This radiographic image comes to a screen 10 via an image processing device 7 and appears there as a normal X-ray shadow image that can be viewed in real time.

In this image it is possible to determine by means of the image processing device 7 or by reading off row markings 11 the cross-section of the body 2 for which computer-tomographic measurements should be carried out. For this purpose a row-selecting device 12 is arranged between the image processing device 7 and an image store 6. In this image store 6 the image points which are produced by the television camera are stored two-dimensionally according to their grey shades. Depending on the number of rows in the television image, the data for from 512 to 1024 layer images can thus be stored simultaneously in the image store 6. By rotating the body 2 by means of the manipulator 13 through successive small angles of 1° to 2° through an angular range of at least 180°, the data necessary for the computer-tomography can be determined and stored in the image store 6. These data subsequently arrive in a computer 8, where they are reconstructed to form a layer image, and led via a further image store 9 to the television screen 10 where they are displayed.

Since the image in the X-ray image amplifier 3 has already been split up into rows by the television camera 5, only rotation of the body 2 is necessary, and not vertical translation.

Figure 2:
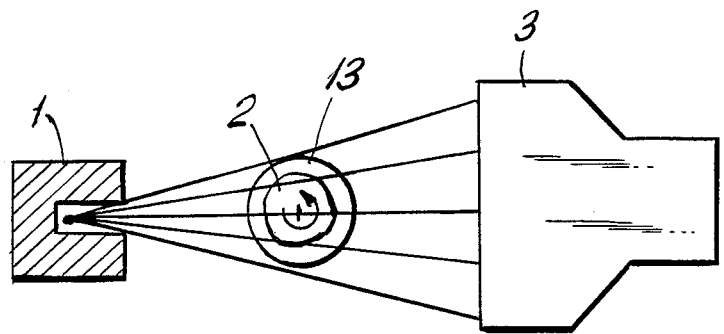
FIG. 2 shows a plan view of the part of the device for producing a radiographic image.
Figure 3:
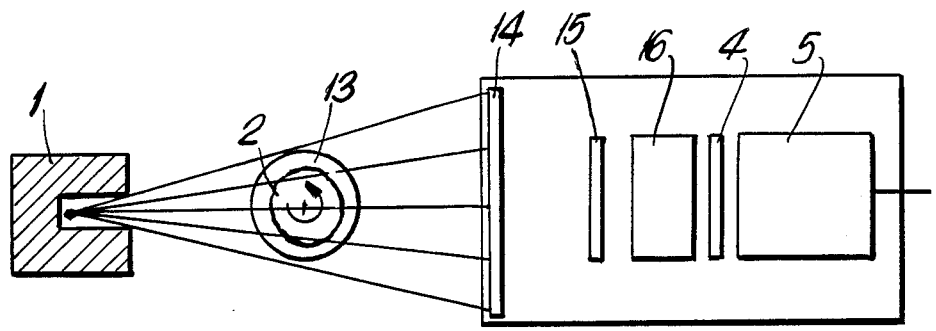
FIG. 3 shows a plan view as in FIG. 2 including an X-ray screen followed by a light amplifier and a television camera and FIG. 4 shows a functional diagram of the device according to the invention with a high resolution row-detector arranged in the beam path.

The device shown in FIG. 3 differs from that shown in FIGS. 1 and 2 only in that the radiographic image appears on an X-ray screen 14 and arrives in the television camera 5 via a lens 15, a light amplifier 16 and a further lens 4. The processing of the image occurs in the same manner as in the device shown in FIGS. 1 and 2.

Figure 4:
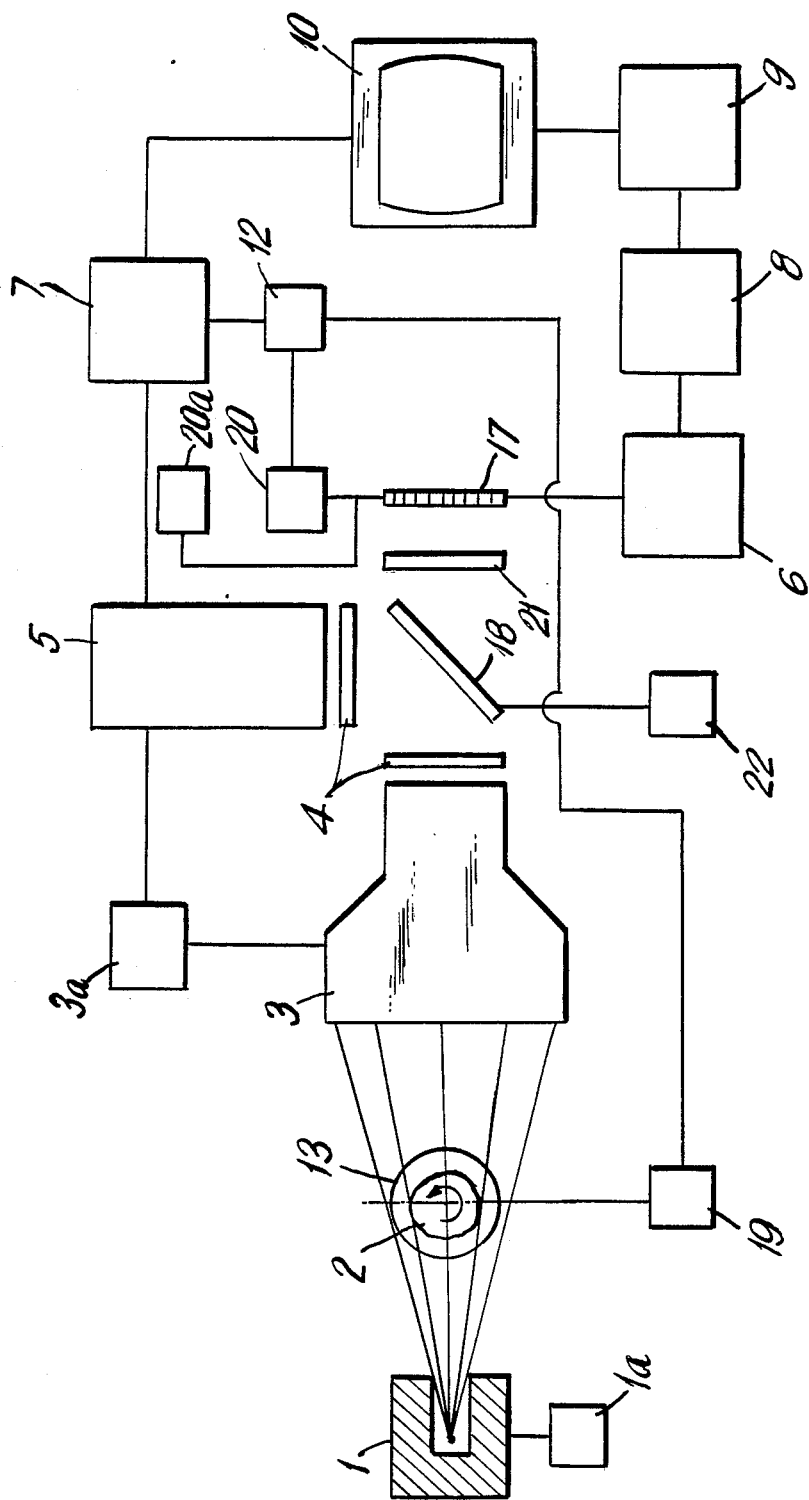

In the device shown in FIG. 4 a semi-transparent or movable mirror 18 is located after the lens 4 behind the X-ray image amplifier 3. The television camera 5 is arranged perpendicular to the beam path of the X-ray image amplifier 3 so that the image falls in the television camera 5 when the mirror 18 is in the position shown. The radiation source 1 has a rotatable and height adjustable manipulator 1a. The pick-up device formed by the x-ray image amplifier 3 and the television camera 5 has a manipulator 3a for effecting rotation relative to the body 2 and adjustment in height.

In the beam path of the X-ray image amplifier 3 a high resolution row-detector 17 is arranged behind a further lens 21. If the mirror 18 is semi-transparent the reflected image falls in the television camera 5 and the transmitted image falls on the row-detector 17. If the mirror 18 is non-transparent it must be turned away by means of a rotary device 22 when the image of the X-ray image amplifier 3 is to fall on the high resolution row-detector 17.

Since the row-detector 17 is intended to capture only one row at a time, i.e. is set to pick up a particular layer image, either the manipulator 13 or the row-detector 17 must have height-adjusting device 19 or 20 respectively. The height-adjusting device 19 or 20 is connected to a row-selecting device 12 which is connected to the image processing device 7. The height adjusting device 19 can also rotate the body 2.

The real-time radiographic image reaches the screen 10 via the X-ray amplifier 3, the mirror 18, the television camera 5 and the image processing device 7, while the computer-tomographic layer image is produced by way of the row-detector 17, the image store 6, the computer 8 and the further image store 9 and is likewise displayed on the screen 10.

Selection of the layer image is done by means of the row-selecting device 12 in the same manner as in the device shown in FIG. 1.

What is claimed is:

1. A device for producing a radiographic image of a body having a source of high-energy radiation arranged on one side of the body and a pick-up device arranged on the other side of the body, and comprising a real-time system for reproducing the radiographic image, a television camera, a screen and a computer-tomograph for evaluation for the radiographic image and for displaying a cross-section of the radiographed body on the screen, and a high ressolution row-detector is arranged in the beam path of the radiographic image.

2. A device according to claim 1, wherein the device for picking up the radiographic image comprises an X-ray image amplifier followed by a television camera.

3. A device according to claim 1, wherein the device for picking up the radiographic image comprises an X-ray screen followed by a light amplifier and a television camera.

4. A device according to claim 1 wherein an image processing device is arranged between the television camera and the screen and a row-selecting device is connected to the image processing device and to means for adjusting the height of at least one of a manipulator for the body, the row-detector, and the radiation source.

5. A device according to claim 1, wherein at least one of the television camera and the row-detector is movable.

6. A device according to claim 1, wherein a movable mirror is arranged between the radiographic image and the television camera or the row-detector.

7. A device according to claim 1, wherein a semi-transparent mirror is arranged in the beam path of the radiographic image to direct the transmitted image towards the television camera and the reflected image towards the row-detector, or vice versa.

8. A device according to claim 1, wherein the radiation source and pick-up device are rotatable relative to the body and adjustable in height.

9. A device according to claim 1 which includes a rotatable and height-adjustable manipulator for the body.

10. A device according to claim 1 which includes a rotatable manipulator for the body and a height-adjusting device for the row-detector and the radiation source.

11. A device according to claim 1, wherein an image store arranged behind the television camera and the computer-tomograph for row-wise evaluation of the image is connected to the image store.

12. A device according to claim 1, wherein there are row markings on the screen and a row-selecting device is connected to means for adjusting the height of a manipulator for the body or of the row-detector.

13. A device according to claim 11, wherein there are row markings on the screen and a row-selecting device is connected to the image store.

14. A device according to claim 11, wherein an image processing device is arranged between the television camera and the screen and a row-selecting device is connected to the image processing device and to the image store.

15. A process for producing a radiographic image of a body by means of a source of high-energy radiation arranged on one side of the body and a pick-up device arranged on the other side of the body in a beam path of the radiographic image, wherein by means of a real-time reproducing system producing a radiographic image on a screen, and with reference to the image displayed selecting a row for displaying a computer-tomographic layer image by inserting a high resolution row-detector in the beam path of the radiographic image, carrying out computer-tomographic readings by rotating the body stepwise, storing and editing the data and reconstructing and displaying the image on a screen.

16. A process according to claim 15, wherein storing image points of the television image in a two-dimensional image store and reconstructing the image points of each row using a computer-tomograph to form a layer image of the selected row.

* * * * *